(12) United States Patent
Hossainy et al.

(10) Patent No.: US 8,246,973 B2
(45) Date of Patent: Aug. 21, 2012

(54) FREEZE-THAW METHOD FOR MODIFYING STENT COATING

(75) Inventors: Syed F. A. Hossainy, Fremont, CA (US); Gordon Stewart, San Francisco, CA (US); Benjamyn Serna, Gilroy, CA (US); Lothar W. Kleiner, Los Altos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 999 days.

(21) Appl. No.: 11/472,760

(22) Filed: Jun. 21, 2006

(65) Prior Publication Data

US 2008/0305141 A1    Dec. 11, 2008

(51) Int. Cl.
*A61F 13/00* (2006.01)
*A61L 33/00* (2006.01)
*B05D 3/02* (2006.01)

(52) U.S. Cl. ................ 424/422; 427/2.1; 427/374.2
(58) Field of Classification Search ................ None
See application file for complete search history.

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,886,062 A | 12/1989 | Wiktor |
| 5,981,826 A | 11/1999 | Ku et al. |
| 6,039,977 A | 3/2000 | Venkatraman et al. |
| 6,458,156 B1 | 10/2002 | Wan et al. |
| 6,908,624 B2 | 6/2005 | Hossainy et al. |
| 8,048,442 B1 | 11/2011 | Hossainy et al. |
| 2001/0053753 A1* | 12/2001 | Engekhart ............ 510/130 |
| 2002/0091437 A1* | 7/2002 | Tseng et al. ............ 623/1.13 |
| 2003/0083740 A1* | 5/2003 | Pathak .............. 623/1.43 |
| 2004/0072922 A1 | 4/2004 | Hossainy et al. |
| 2004/0098076 A1 | 5/2004 | Rolando et al. |
| 2004/0177805 A1* | 9/2004 | Hijlkema et al. ........ 118/101 |
| 2004/0220665 A1* | 11/2004 | Hossainy et al. ......... 623/1.42 |
| 2005/0070997 A1 | 3/2005 | Thornton et al. |
| 2005/0109158 A1* | 5/2005 | Keener ................. 75/352 |
| 2005/0131201 A1* | 6/2005 | Pacetti et al. ............ 528/272 |
| 2005/0154450 A1* | 7/2005 | Larson et al. ............ 623/1.42 |
| 2005/0288481 A1 | 12/2005 | Des Noyer et al. |
| 2006/0018948 A1* | 1/2006 | Guire et al. ............ 424/426 |
| 2006/0035011 A1 | 2/2006 | Stenzel |
| 2006/0078588 A1 | 4/2006 | Hossainy |
| 2006/0196073 A1* | 9/2006 | Parker .................. 34/62 |
| 2006/0246109 A1 | 11/2006 | Hossainy et al. |
| 2007/0202323 A1* | 8/2007 | Kleiner et al. ............ 428/336 |
| 2007/0280988 A1 | 12/2007 | Ludwig et al. |
| 2008/0124372 A1 | 5/2008 | Hossainy et al. |
| 2011/0086162 A1 | 4/2011 | Hossainy et al. |
| 2011/0151104 A1 | 6/2011 | Kleiner et al. |
| 2011/0153004 A1 | 6/2011 | Kleiner et al. |
| 2011/0200660 A1 | 8/2011 | Kleiner et al. |

FOREIGN PATENT DOCUMENTS

| | | |
|---|---|---|
| WO | WO 2004/112863 | 12/2004 |
| WO | WO 2007/112305 | 10/2007 |

OTHER PUBLICATIONS

Kell Journal of Applied Polymer Science 1960 IV:252.*
Kuribayashi et al. Materials Science Engineering A Mar. 2006 419:131-137.*
Dry (2001). In Chambers 21st Century Dictionary. Retrieved from ttp://www.credoreference.com/entry/chambdict/dry.*
Elsner et al. American Journal of Cardiology 1999 84: 335-338.*
International Search Report for PCT/US2007/014496, filed Jun. 20, 2007, mailed Jan. 28, 2008, 12 pgs.
European Search Report for 07 796 336.1-2107, mailed Nov. 11, 2009, 4 pgs.
Lazzeri et al., "Physico-chemical and mechanical characterization of hydrogels of poly(vinyl alcohol) and hyaluronic acid", J. of Mat. Science Mat. In Medicine 5, pp. 862-867 (1994).
Peppas et al., "Reinforced uncrosslinked poly(vinyl alcohol) gels produced by cyclic freezing-thawing processes: a short review", J. of Controlled Release 16, pp. 305-310 (1991).
U.S. Appl. No. 10/807,546, filed Mar. 22, 2004, Syed F.A. Hossainy et al.

* cited by examiner

*Primary Examiner* — Juliet Switzer
*Assistant Examiner* — Caralynne Helm
(74) *Attorney, Agent, or Firm* — Squire Sanders (US) LLP

(57) ABSTRACT

Methods are disclosed for controlling the morphology and the release-rate of active agent from a coating layer for medical devices comprising a polymer matrix and one or more active agents. The methods comprise exposing a wet or dry coating to a freeze-thaw cycle. The coating layer can be used for controlled delivery of an active agent or a combination of active agents.

19 Claims, 1 Drawing Sheet

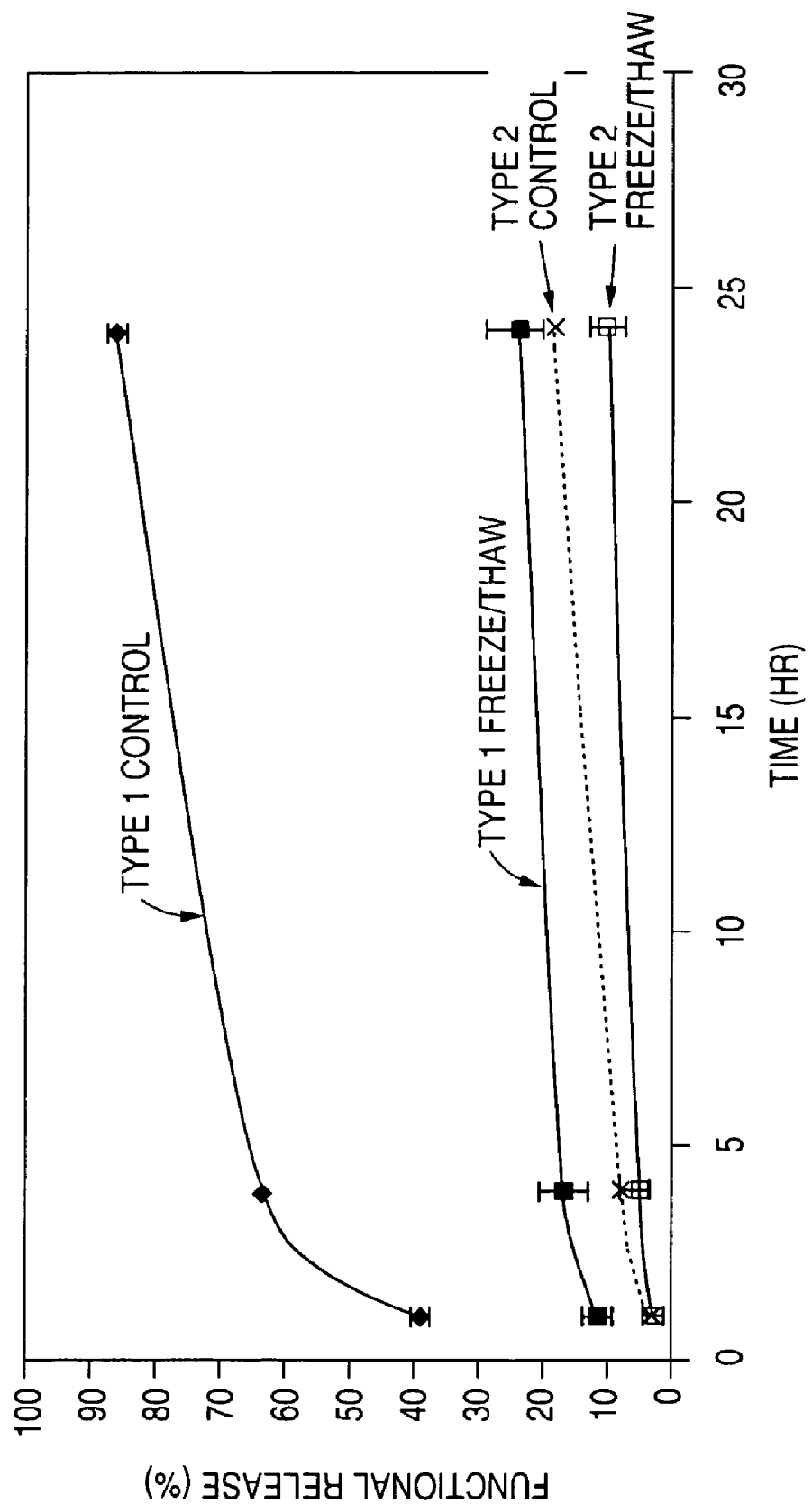

FREEZE-THAW METHOD FOR MODIFYING STENT COATING

TECHNICAL FIELD

The present invention relates generally to the field of medical devices, particularly implantable medical devices, and to methods for coating such devices with layers comprising a polymer matrix and one or more active agents. More particularly, this invention pertains to methods for controlling the morphology of coating layers. This invention further pertains to methods for designing and controlling active agent release-rates from coating layers for medical devices.

BACKGROUND

In the area of medical devices, biomaterial research continues to search for new compositions and methods to improve and control the properties of the medical devices. This is particularly true for medical articles that are implantable within a subject, where predictable and controllable performance is essential to the successful treatment of a subject.

An example of an implantable medical device is a stent. Stents can act as a mechanical means to physically hold open and, if desired, expand a passageway within a subject. Typically, a stent is compressed, inserted into a small vessel through a catheter, and then expanded to a larger diameter once placed in a proper location. Stents play an important role in a variety of medical procedures such as, for example, percutaneous transluminal coronary angioplasty (PTCA), a procedure used to treat heart disease by opening a coronary artery blocked by an occlusion. Stents are generally implanted in such opening a coronary artery blocked by an occlusion. Stents are generally implanted in such procedures to reduce occlusion formation, inhibit thrombosis and restenosis, and maintain patency within vascular lumens. Examples of patents disclosing stents include U.S. Pat. Nos. 4,733,665; 4,800,882; and 4,886,062.

Stents are also being developed to locally deliver active agents, e.g. drugs or other medically beneficial materials. Local delivery is often preferred over systemic delivery, particularly where high systemic doses are necessary to affect a particular site. For example, agent-coated stents have demonstrated dramatic reductions in stent restenosis rates by inhibiting tissue growth associated with restenosis.

Proposed local delivery methods from medical devices include coating the device surface with a layer comprising a polymeric matrix and attaching an active agent to the polymer backbone or dispersing, impregnating or trapping the active agent in the polymeric matrix. For example, one method of applying an active agent to a stent involves blending the agent with a polymer dissolved in a solvent, applying the composition to the surface of the stent, and removing the solvent to leave a polymer matrix in which an active agent is impregnated, dispersed or trapped. During evaporation of the solvent, phase separation can disadvantageously occur, often resulting in hard-to-control process conditions and a drug coating morphology that is difficult to predict and control. This makes delivery of the agent unpredictable.

Further, manufacturing inconsistencies among different stents can arise with the above coating method. For example, release-rate variability has been observed among supposedly identical stents made by the same process. Apparently, when some polymer coatings comprising active agents dry on the surface of a medical device different morphologies develop in different coatings, even if the coating process parameters are consistent. These differences in coating morphology may cause active agent release-rates from different stents to vary significantly. As a consequence of the inconsistent release-rate profiles among stents there can be clinical complications. Thus, there is a need for methods that can control the variability of active agent release-rates among medical devices and provide manufacturing consistency.

Morphological changes that affect release-rates of active agents have been observed to be dependent on the active agent phase in the polymer matrix. When a coating composition is applied to the surface of a medical device the active agent is initially evenly dispersed in the coating composition. However, during processing the agent may migrate or phase separate to form different phase regions within the coating layer. These regions are often connected with each other and are referred to as the percolation phase. The mass transport properties of active agents are distinct through the percolation phase. Mass transport through the percolation phase is driven by the solubility of active agent in the release medium, the diffusivity of the active agent in the release medium, and the morphological feature of the percolated phase such as, for example, tortuosity and area fraction. The release-rate of the active agent is often greatly increased from these regions or phases. The formation of percolated phases is particularly pronounced at high active agent concentrations, for example above about 35% by volume fraction of active agent to polymer in the coating layer. The actual volume percent will vary and depends greatly on the aspect ratio and morphology of the active agent as well as the nature of the surrounding polymer.

Those skilled in the art will therefore appreciate that local delivery would benefit not only from improved release-rate profiles that are controlled and predictable, but also from manufacturing improvements that would provide consistency. Thus, methods for making coated medical devices with more reliable performance are highly desirable and essential to providing effective treatment of patients. In addition, control over the release-rate can assist in designing and maintaining the physical and mechanical properties of medical devices and coatings, as well.

SUMMARY

Methods are disclosed for controlling the morphology and the release-rate of active agent from coating layer(s) for medical devices comprising a polymer matrix and one or more active agents. The methods comprise exposing a wet or dry coating to a freeze-thaw cycle. The coating layer(s) can be used for controlled delivery of an active agent or a combination of active agents. In accordance with one embodiment, the method comprises (a) preparing a coating composition comprising one or more polymers, one or more solvents and optionally one or more therapeutic agents; (b) applying the coating composition onto a medical device to form a wet coating layer; and (c) subjecting the wet coating layer to a freeze-thaw cycle.

The freeze part of the cycle can comprise dipping the medical device in liquid nitrogen. In some embodiments, at least an amount of the solvent(s) can be removed prior to the freeze-thaw cycle.

In accordance with another embodiment, the method comprises (a) preparing a coating composition comprising one or more polymers, and one or more solvents and optionally one or more active agents; (b) applying the coating composition onto a medical device to form a wet coating layer; (c) removing the solvent(s) to form a dry coating layer, the dry coating layer having less than 2% solvent(s); and (d) subjecting the dry coating layer to a freeze-thaw cycle.

In accordance with another embodiment, the coating on the device is subjected to a freeze-thaw cycle using an oven or chamber with temperature control and temperature cycling capabilities.

BRIEF DESCRIPTION OF THE DRAWING

FIG. 1 is a graph showing a release rate profile according to the Example.

DETAILED DESCRIPTION

As discussed in further detail below, the present invention generally pertains to coating layer or layers for medical devices, particularly implantable medical devices, comprising a polymer matrix and one or more active agents. The present invention also provides methods for forming coating layer(s) for medical devices comprising a polymer matrix and one or more active agents, where it is believed that the morphology of the coating layer and/or the phase state of the active agent within the layer are controlled by process parameters. Further, the present invention pertains to methods for controlling the morphology of a coating layer and/or the release-rate of an active agent from the layer.

It is believed that by controlling the morphology of the coating layer during formation, and particularly the active agent phase state within it, the release-rates of the active agent from the coating layer can be more effectively controlled and manufacturing inconsistencies reduced or eliminated. Thus, improved therapeutic, prophylactic or other biological effects may be realized in the treatment of a subject. The use of process parameters in the methods of the present invention instead of additional excipients to control active agent release-rates provides advantages in the design of controlled release systems. Further, the control of active agent release-rates has positive implications for the mechanical integrity of the polymeric matrix, as well as a relationship to a subject's absorption rate of absorbable polymers.

There are many considerations in designing, controlling or predicting the active agent release-rates from a coating layer comprising a polymer matrix and one or more active agents. These include, but are not limited to, the morphology of the coating layer and components in the layer; the size and shape of the active agent; the active agent phase and the distribution of phases in the layer; the selection and the concentration of active agent or agents; the presence of polymorphism of the agents; the polymer or polymers forming the polymer matrix; the presence of functional groups on the polymers; the hydrophilicity or hydrophobicity of the polymer matrix; the presence of other additives in the composition, for example, fillers, metals, plasticizing agents, cross-linking agents; and the degree, if any, of bonding between the polymer matrix and the active agent(s).

The morphology of the coating layer is particularly important in determining the performance characteristics of the coating layer, because the distribution of an active agent and the phases of the active agent within the polymer matrix directly relate to the active agent release-rate profile. In particular, a goal is controlling the polymer-matrix-active-agent morphology within the coating layer(s) to provide layer(s) with predictable active agent release-rates. It is believed that the methods of the present invention use process parameters to control coating layer morphology and phase state of the active agent in the polymer matrix. The methods of the present invention can decrease active agent release-rates. A further aspect of the present invention provides methods for enhanced process control and coating reproducibility for medical articles and devices comprising a polymer matrix and one or more active agents.

The term "morphology" as used herein refers to the way in which a polymer matrix, optionally active agent(s), and optionally other components, lie in a coating layer after solvent removal. The morphology can be defined in terms of properties such as the shape, structure, form or phase of components in the coating layer. The term "configuration" is also used herein to refer to the morphology of the coating layer. In particular, morphology is used herein to describe the arrangement of the phase(s) or phase state or distribution of the active agent in the polymer matrix and the distribution of those phases within the coating layer.

The morphology of the coating layer can be defined, for example, by the presence and characteristics of phase separation between components within the coating, where the phase separation can exist between polymers of the matrix, an agent and a polymer, between agents, or between other components in the polymeric matrix. In one embodiment, the coating layer morphology is defined by the phase state or distribution, or phase(s) of the active agent within the polymer matrix. In other embodiments, the morphology can be defined, for example, by the characteristics of the zone of phase separation, where the zone of phase separation can be thin, thick, continuous, non-continuous; hydrophobic, hydrophilic, porous, interconnected, dispersed, and the like. In some embodiments, the morphology can be defined, for example, by other physical characteristics of the polymeric matrix including, but not limited to, the presence of pores, crystalline or semi-crystalline regions, amorphous regions, metals, ceramics, the existence of polymorphism in agents, and the like. Any coating property that would be considered a morphological characteristic to one of skill in the art is within the scope of the present invention. The morphology can be characterized by any method or measurement known in the art to characterize layers comprising polymers.

The "phase" of components of the coating layer can be defined by the crystallinity, semi-crystallinity, liquid crystallinity, orientation, or polymorphic state of the component, for example. The term "phase state" is used to refer to the phases of a component in the coating layer, particularly when the component is present in more than one phase. In particular, phase state is used to refer to the phase distribution of active agent in a coating layer. In one embodiment, the phase state of the active agent in the coating layer comprises one or more phases.

The formation of an active agent phase depends on the thermodynamics and kinetics of processing. Kinetics of processing can be further subdivided into internal kinetic time constants and external time constants. Internal time constants include, for example, crystallization and migration rate of active agents. External time constants include, for example, the rate of solvent removal from the wet coating layer.

The methods and embodiments of the present invention are most useful where the active agent is blended with, dissolved in, impregnated, trapped or distributed in the polymer matrix. This means the active agent exists molecularly, at a molecular size, surrounded by polymer molecules of the polymer matrix. In some of these types of embodiments, the active agent is not covalently attached to the polymer matrix. The release, and hence the release-rate, of the active agent from the coating layer depends on the ability of the active agent to diffuse through the polymer matrix. This diffusion depends on the active agent phase in the layer and the transport properties of the polymeric matrix. It is one of the goals of the present invention to modulate or control the active agent phase and hence control the release-rate of the active agent from the coating layer.

In some embodiments, the active agent exists in the coating layer in a dissolved, dispersed or percolated phase. A coating layer can comprise some fraction of all three active agent phases. Without being bound by any particular theory, it is believed that the ratio of the co-existing phases is a function of the volume fraction of active agent to polymer in the coating layer, as well as the active agent's physicochemical properties, such as its solubility in the polymer matrix. Thus, at low active-agent-to-polymer ratios, for example below about 10% by volume fraction active agent to polymer, the active agent phase will predominantly be a dissolved phase. As the percentage of active agent increases, the fraction of the other phases mixed with the dissolved phase increases.

In one embodiment, the active agent of the coating layer is in a dissolved phase. In one embodiment, the active agent of the coating layer is in a dispersed phase. In one embodiment, the active agent of the coating layer is in a percolated phase. In one embodiment, the active agent of the coating layer comprises a mixed phase, wherein the phase state comprises two or more phases selected from the group consisting of dissolved, dispersed, or percolated phases. In one embodiment, the active agent phase state comprises dissolved phase, dispersed phase and percolated phase. In one embodiment, the active agent phase state is primarily dissolved phase. In one embodiment, the active agent phase state is primarily dispersed phase. In one embodiment, the active agent phase state is primarily dissolved and dispersed phases. The percentage of an active agent phase present in a coating layer can be controlled by the methods described herein.

As used herein, dissolved phase refers to an active agent phase in which the active agent is dissolved in the solid polymer matrix as in a solid solution. In other words, the active agent species are not closely associated with other active agent species within the coating layer and are surrounded by polymer molecules of the polymer matrix. Dissolved phases occur particularly at low active agent concentrations, where the concentration is measured as a volume fraction of the active agent to polymer in the coating layer— for example at concentrations below about 10% by volume fraction of active agent to polymer in the coating layer, and also in coating layers where no phase separation occurs between the solvent, polymer matrix and active agent. Additionally, the presence of dissolved phase depends on the active agent solubility in polymer matrix polymers. At higher volume fractions, the dissolved phase usually co-exists with other active agent phases. In one embodiment, the amount of dissolved phase in the coating layer is equal to or greater than the amount of either dispersed or percolated phase. The phase ratios depending on, for example, the active agent concentration, the degree of phase separation, and the active agent solubility in polymer matrix polymers.

At active agent concentrations of about 10% or greater by volume fraction of active agent to polymer the active agent may coalesce to form a dispersed phase. As used herein, a dispersed phase refers to a phase where a number of active agent species coalesce to form active agent particles or clusters throughout the coating layer that are surrounded by polymer matrix polymer molecules. Dispersed phases can also form at lower concentrations depending on the solubility of active agent in the polymer matrix.

As used herein, percolated phase refers to an active agent phase where active agent molecules significantly migrate and/or phase separate in the polymer matrix during formation of the coating layer forming connected pathways of active agent throughout the polymer. When the active agent is present in the percolated phase, there is less control over the active agent release-rate than when the active agent is in the dissolved or dispersed phase, because the random connected pathways of active agent provide a means for the active agent to diffuse out of and be released from the coating layer. Thus, the presence of percolated active agent phase has a significant effect on the release-rate of the active agent from the coating layer. The presence of percolated phase increases the active agent release-rate. The mass transport properties of active agents are distinct through the percolation phase. The mass transport through the percolation phase is driven by the solubility of active agent in the release medium, the diffusivity of the active agent in the release medium, and the morphological feature of the percolated phase such as, for example, tortuosity and area fraction. The percolated phase is most often observed at active agent concentrations of about 35% or greater by volume fraction of active agent to polymer in the coating layer, but may also form at lower concentrations depending on the solubility of the active agent in the polymer matrix and other factors such as active agent aspect ratio or morphology and active agent-polymer interfacial properties. The active agent concentration at which percolated phase becomes the predominant phase is referred to herein as the "percolation threshold." The active agent concentration at which the percolation threshold is observed depends on factors including, for example, the choice of active agent, polymer matrix and solvent, as well as those described below. In some embodiments of the present invention, the concentration of active is at the percolation threshold and the active agent is primarily in a phase other than the percolated phase.

Percolate phase formation kinetics depend on a number of factors including the active agent concentration, the solvent phase, the solvent used, the mobility of active agent, the temperature at which solvent is removed, the method of removing solvent and other processes conditions, such as the environment in which drying occurs. By using the methods described herein to fix the active agent phase in a desired phase or phase state before solvent removal, the degree of phase separation and dispersion of active agent within the polymer matrix can be controlled. Thus, a phase state profile and morphology of the coating layer can be created that provides a controllable release-rate profile for the active agent. Further, by fixing the active agent in a dissolved or dispersed phase at higher active agent concentrations more control on the release-rate is obtained because formation of percolated phase is prevented or greatly reduced. In one embodiment, percolated phase formation kinetics at high active agent concentrations are controlled by fixing the active agent phase state after coating a device with a coating composition. Another aspect of the present invention is to control or prevent concentration gradients of active agents from forming in the coating layer, by fixing the active agent phase state before removing solvent from the wet coating layer.

The coating layer or layers of the present invention comprise a polymer matrix, including one or more polymers and one or more active agents. Optionally, the coating layer may further comprise one or more additives or other components. In addition to the polymer/drug layer, the coating layers can include any number of other layers including primer layer, other drug/polymer layer(s), topcoat layer or finishing coating or any combination of these layers.

The drug coating layer(s) can be formed by blending one or more active agents together with one or more polymers dissolved in one or more solvents to form a coating composition, applying, such as by spraying or dipping, the coating composition to a medical device surface or onto a primer layer, and removing the solvent(s) to leave on the device active agent(s) dispersed in a polymer matrix. The morphology of the coating layer comprising a polymer matrix and one or more agents, and the phase state of the active agent within that layer, and hence the agent release-rate from the layer, can be profoundly affected by the manner in which the coating layer is formed and the solvent is removed from the coating composition to form a coating layer. When solvent is removed during drying, active agent dispersion and configuration within the coating layer can change due to phase separation between the solvent, and the polymer and active agent phase. This results in a coating layer morphology and distribution of active agent that is difficult to predict and control.

One embodiment of the present invention provides methods to control the coating layer morphology by fixing the active agent morphology before, during and or after solvent removal from the coating composition. In some of these embodiments, solvent removal forms a dried coating layer. Dried coating is defined as less that 2% residual solvent. In some embodiments, it is defined as less than 1% residual solvent. In some embodiments, it is defined as 0% solvent, i.e., all of the solvent is completely removed. Yet in some embodiments, dried coating can include an insignificantly nominal amount of solvent remaining, such as 0.1% or less.

The coating composition after being deposited on a device surface is referred to as a "wet coating layer." As used herein the term "wet coating layer" refers to a coating composition comprising solvent that has been applied to the device. "Wet" can be defined as opposite of the dry coating as defined above or, in other words, a coating layer is referred to as wet until essentially all the solvent is removed from the coating layer. In some embodiments, wet is defined as including all of the solvent (100%) or over 90% of the solvent. In some embodiments, it is defined as including over 80%, 70%, 60% or 50% ("majority") of the solvent. In the embodiments of the present invention, solvent in a wet coating layer may not necessarily be in a liquid state. In one embodiment, the method of the present invention is conducted when the coating is wet, when the coating is dry, or at each step. In other embodiments, a fraction of solvent is removed before the morphology of the polymer matrix and active agent is fixed. This removal helps modulate the degree of phase separation and the distribution of active agent phases in the layer, and hence helps control the active agent release-rate. The present invention is especially useful for compositions with a high active-agent-to-polymer ratio, where phase separation or percolated phase formation are more likely. The methods of the present invention may further control or modulate the development of active agent concentration gradients within the polymer matrix.

It is believed that the coating layers provide for less variable release-rates of active agents from the coatings layers. While not being bound by any theory, apparently the fixing process renders the coating layer's thermo-mechanical and morphological properties less sensitive to subsequent processing. Apparently, controlling coating layer morphology, and hence active agent release-rates, can control or eliminate manufacturing inconsistencies.

Methods of Forming Coating Layers

The present invention provides methods for forming a coating layer for a medical device with a controlled active agent morphology. In one invention embodiment, fixing the active agent phase state while forming the coating layer controls the active agent release-rate. In some embodiments, controlling the release rate means reducing the release rate as compared to if the modification was not performed on the coating.

In some embodiments of the present invention, the method comprises:
(a) preparing a coating composition comprising one or more polymers, one or more active agents, and one or more solvents;
(b) applying the coating composition onto a medical device to form a wet coating layer;
(c) subjecting the wet coating layer to a freeze-thaw cycle; and
(d) removing the one or more solvents from the wet coating layer to form a coating layer.

In some embodiments of the present invention, the method comprises:
(a) preparing a coating composition comprising one or more polymers, one or more active agents, and one or more solvents;
(b) applying the coating composition onto a medical device to form a wet coating layer;
(c) removing a fraction of the one or more solvents from the wet coating layer;
(d) subjecting the wet coating to a freeze-thaw cycle; and
(e) removing the remaining solvent(s) to form a coating layer.

In some embodiments of the present invention, the method comprises:
(a) preparing a coating composition comprising one or more polymers, one or more active agents, and one or more solvents;
(b) applying the coating composition onto a medical device to form a wet coating layer;
(c) removing the solvent(s) to form a dry coating layer; and
(d) subjecting the dry coating layer to a freeze-thaw cycle.

The various embodiments described above can include applying one or more polymer layers, with or without a drug, over the layer including the one or more agents such that the freeze-thaw cycle is performed before and/or after the formation of such layers. Embodiments of the present invention may further comprise one or more optional post-formation process steps. For example, post-formation process steps include, but are not limited to, annealing the coating layer, applying an optional finishing coat layer, and sterilization. Other post-process steps or combinations of post-process steps may also be used in the practice of the invention.

The freeze-thaw cycle comprises applying a cold liquid to the wet or dry coating following by heating the coating. The freeze part of the cycle can be conducted by a cold inert gas or fluid such as liquid nitrogen, dry ice ($CO_2$), liquid argon, or liquid ammonia. The gas can be discharged onto the coating or the coating can be dipped into a container of the liquid. Freeze-thaw cycling can be successfully conducted in temperature cycling ovens or chambers which are hooked up to liquid nitrogen storage tanks and have the necessary elements to change from very cold to very hot temperatures with excellent temperature control capabilities. In this way, hundreds or thousands of stents can be subjected to the regimen at one time. Minimum or no physical contact, such as by a substrate, a part of a device, molding or apparatus, with the coating is desired to prevent damage to the coating. In a preferred embodiment, the wet or dry coating on the device is dipped into a container of liquid nitrogen. The coating composition can be cooled to a temperature of 10° C. or less, alternatively 0° C. or less, −10° C. or less, −20° C. or less, −30° C. or less, −40° C. or less, −50° C. or less, −100° C. or less, −150° C. or less, and −180° C. or less. In some embodiments, the temperature has to be equal or below the freezing temperature of a solvent used. The duration of exposure can be from 1 second to 5 minutes. In some embodiments, it can be less than 1 minute. In some embodiments, it can be from 1 second to 30 seconds.

The thaw portion of the cycle can be conduct by placing the device in an oven or by applying a warm gas to the device. The gas can be air, nitrogen or an inert such as argon. For the application of the gas, it is preferred that the gas be applied evenly across the surface of the device. For stent applications, this can be accomplished by controlling the distance of the gas nozzle from the stent and rotation of the stent during the gas application process. The temperature during the thaw portion of the cycle can be from about 25° C. to 300° C. In some embodiments, it should be not more than 150° C., not more than 100° C., not more than 75° C., or not more than 50° C. In some embodiments, the temperature can be 50° C.+/−3° C. The duration of the thaw cycle can be from 10 seconds to 2 hours. In some embodiments, it can be less than 1 minute, such as 30 seconds. The freeze-thaw cycle can be a single cycle or multiple cycles such as 2 or 3 cycles. In some embodiments, the condensation formed on the coating should be removed such as by physically agitating the stent by motions including taping, shaking or the like. Condensation can be removed during and/or after the thaw portion of the cycle.

When the freeze-thaw cycle is applied to a wet coating, subsequent sublimation or other suitable methods can be used to remove any remaining solvent.

Another aspect of the present invention is to control the fraction of solvent removed from the wet coating layer before the freeze-thaw cycle. By removing a known solvent fraction after applying the coating composition, the morphology of the polymer-matrix-active-agent coating layer can be designed to have a selected amount of phase separation between the solvent and the polymer matrix and active agent phase, and thus a predetermined fraction of an active agent phase. Hence, the active agent release-rate can be modified for the most beneficial therapeutic effect in a subject. In some embodiments, between about 1 and 90%, alternatively, between about 1 and 80%, about 1 and 70%, about 1 and 60%, about 1 and 50%, about 1 and 25%, or about 1 and 10%, by weight of the solvent in the coating composition is removed from the coating layer before the polymer-matrix-active-agent configuration in the coating layer is subjected to the freeze-thaw cycle.

The percentage of an active agent phase present in a coating layer can be selected by the methods described herein. The amount of a particular active agent phase present in the coating layer can vary considerably over the range from 0% to 100% based in the total amount of active agent in the coating layer. In some embodiments, the ratio of polymer:drug (w/w) can range from 50:1 to 1:50. In some embodiments the following polymer:drug ranges are applicable: 1:1; 2:1; 3:1; 4:1; 5:1; 6:1: 7:1; 8:1; 9:1; 10:1; 1:2; 1:3; 1:4; 1:5; 1:6; 1:7; 1:8; 1:9; 1:10; or between any combination of such ranges. In one embodiment, the percentage of dissolved phase is greater than the combined amount of dispersed and percolated phase. In other embodiments, the percentage of dissolved phase is equal to or greater than the percentage of either dispersed or percolated phase in the coating layer. In yet other embodiments, the percentage of dissolved phase is less than the percentage of dispersed or percolated phase in the coating layer. Designing the percentage of active agent in different phases can select the most therapeutically effective release-rate. In some embodiment, the release-rate profile of active agent from the coating layer is determined by the ratio of the phase states of the active agent in the coating layer.

Coating layer thickness is from about 0.1 nm to about 1.0 cm, from about 0.1 nm to about 1.0 mm, from about 0.1 nm to about 100 µm, from about 0.1 nm to about 1 µm, from about 0.1 nm to about 100 nm, from about 0.1 nm to about 10 nm, from about 10 nm to about 100 nm, from about 0.5 µm to about 10 µm, from about 1 µm to about 10 µm, from about 10 µm to about 50 µm, from about 50 µm to about 100 µm, or any range therein. In other embodiments, the thickness of the coating layer can be regionally distributed throughout a device to create a variation in thicknesses such as, for example, the variation in thicknesses present in an abluminally-coated drug-eluting stent (DES) system.

Coating Compositions

The coating compositions of the present invention comprise one or more active agents (optional for example for topcoat modification), one or more polymers, and one or more solvents. Optionally, the coating composition may further comprise one or more additives or other components such as, for example, plasticizing agents, metals, metal oxides or ceramics.

Coating compositions are prepared by conventional methods, wherein all components are combined and then blended. More particularly, adding a predetermined amount of polymer to a predetermined amount of a compatible solvent forms a polymer solution. The polymer can be added to the solvent at ambient pressure, and under anhydrous or other atmosphere. If necessary, gentle heating and stirring or mixing can cause the polymer to dissolve into the solvent, for example, 12 hours in a 60° C. water bath.

Sufficient amounts of active agent are dispersed in the blended polymer solution. The active agent preferably should be in true solution or saturated in the blended composition. If the active agent is not completely soluble in the composition, operations including mixing, stirring, or agitation can be employed to homogenize the residuals. Alternatively, active agent can first be added to a compatible solvent before mixing with the polymer solution. Optionally, a second solvent, such as tetrahydrofuran or dimethylformamide, can be used to improve the solubility of an active agent in the coating composition or to increase the composition's wetting ability. The second solvent can be added to the coating composition or the active agent can be added to the second solvent before mixing with the polymer solution.

If additives and other components, for example cross-linking agents, plasticizers, or ceramics, are used these may be added and blended with the coating composition at any step.

The amount of active agent in the coating layer should be the dosage or concentration required to produce a therapeutic effect, and greater than the level at which non-therapeutic results are obtained. The dosage or concentration of the active agent depends upon factors such as, for example, the particular circumstances of the subject, the nature of the trauma, the nature of the therapy desired, the time over which the ingredient administered resides at the vascular site, and if other bio-active substances are employed, the nature and type of the substance or the combination of substances. The therapeutically effective dosage can be determined by methods known in the art, such as for example, conducting suitable in vitro studies.

The one or more polymers of the polymer matrix can comprise from about 0.1% to about 35%, and more narrowly from about 2% to about 20% by weight of the total weight of the coating composition. The one or more solvents may comprise from about 19.8% to about 99.8%, more narrowly from about 49% to about 87%, and yet more narrowly from about 79% to about 87% by weight of the total weight of the coating compositions. The one or more active agents may comprise from about 0.02% to about 40%, preferably from about 0.1% to about 9%, and more narrowly from about 0.7% to about 1.2% by weight of the total weight of the coating composition. Selection of a specific weight ratio of the polymer and solvent depends on factors such as, but not limited to, the material from which the device is made, the geometrical structure of the device, and the type and amount of active agent employed. The specific weight percent of active agent depends on the polymer matrix-active agent morphology of the coating layer and phases of active agent required, and factors such as the dosage, duration of the release, cumulative amount of release, and the release-rate desired.

The coating layers of the present invention comprise a polymer matrix, composed of one or more polymers. The one or more polymers comprising the polymer matrix may be in mixed, blended or conjugated form. The polymer matrices and coating compositions of the present invention may also be used to form medical devices by a process such as, for example, molding.

There is a wide choice of polymer and copolymers for use in the polymer matrix of the present invention. The chosen polymer matrix must be one that is biocompatible and minimizes irritation when implanted. The choice of the matrix components depends on numerous factors including, but not limited to, the interactions between the polymer(s) and the agent(s) and/or solvent(s), the biocompatibility of the polymer(s), and the physical, mechanical, chemical and biological properties of the polymers. Performance parameters include, for example, the ability to adhere to the surface of the medical device, the toughness of the coating desired, the capacity for the loading concentration of an agent, and the rate of biodegradation and elimination of the composition from a subject.

Each of the one or more polymers chosen for the matrix can be either biostable or biodegradable. "Biodegradable" refers to polymers that are capable of being completely degraded and/or eroded when exposed to bodily fluids such as blood and can be gradually resorbed, absorbed and/or eliminated from the subject. The term biodegredable is used interchangeably with bioerodable and bioabsorbable. The process of breaking down and eventual absorption and elimination of the polymer can be caused by, for example, hydrolysis, metabolic processes, bulk or surface erosion, and the like. After biodegradatiou traces or residual polymer may remain on the device or near the device. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the polymer matrix releases active agent during biodegradation. In other embodiments, the polymer matrix releases active agent without biodegradation of the matrix. In yet other embodiments, the release of active agent may be partially dependent on biodegradation of the polymer matrix. Biostable polymers should have a relatively low chronic tissue response.

The polymers useful for the polymer matrixes of the present invention include, but are not limited to, natural or synthetic polymers, condensation polymers, homopolymers and copolymers or any combination and/or blend thereof. Polymers may be hydrophobic, hydrophilic, or a combination thereof. Copolymers may be random, alternating, block, graft, and/or crosslinked, and may include polymers with more than two different types of repeating units such as terpolymers. In some embodiments, the polymers are selected such that they specifically exclude any one or any combination of any of the polymers taught herein.

Representative examples of polymers that can be used in the polymer matrices and coating compositions of the present invention include, but are not limited to, poly(acrylates) (such as poly(methacrylates), polymethyl methacrylate and polybutyl methacrylate), acrylic polymers and copolymer (such as polyacrylonitrile), poly(cyanoacrylates), fluorinated polymers or copolymers (such as polyfluoro-alkylenes, polyvinylidene fluoride-co-hexafluoropropene and polytetrafluoroethylene), polycaprolactones, polylactides, poly(D-lactides), poly(L-lactides), poly(D,L-lactides), Poly(lactic acids), poly (glycolic acid), poly(lactide-co-glycolide), poly(glycolic acid-co-trimethylene carbonate), poly(lactic acid-co-trimethylene carbonate, poly(amino acids), polyhydroxyalkanoates, poly(hydroxyvalerate), polyhydroxybutyrates, poly(hydroxybutyrate-co-valerate), polymers and copolymers of hydroxyl ethyl methacryate, polydioxanones, polyorthoesters, polyanhydrides, polyphosphoesters, polyphosphoester urethanes, polyphosphazenes, polycarbonates, polyiminocarbonates, polytrimethylene carbonates, co-poly (ether-esters) (such as polyethylene oxide/polylactic acid (PEO/PLA)), poly(alkylene oxalates), polyurethanes, silicones, polyesters, polyolefins (such as polyethylene and polypropylene), poly(isobutylene) and ethylene-alphaolefin copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), ethylene vinyl alcohol copolymers (such as ethylene vinyl alcohol co-polymer, commonly know by the generic name EVOH or by the trade name EVAL), polyamides (such as Nylon 66 and polycaprolactam), alkyd resins, polyoxymethylenes, polyimides, polyester amides, polyethers including poly(alkylene glycols) (such as poly (ethylene glycol) and poly(propylene glycol)), poly(tyrosine derived carbonates), poly(tyrosine derived arylates), epoxy resins, rayon, rayon-triacetate, biomolecules (such as fibrin, fibrinogen, starch, cellulose, collagen, hyaluronic acid), poly (N-acetylglucosamnine) (chitin), chitosan, cellulose, cellulose acetate, cellulose butyrate, cellulose acetate butyrate, CELLOPHANE, cellulose nitrate, cellulose propionate, cellulose ethers, and carboxymethyl-cellulose, and derivatives, copolymers and combinations of the foregoing. In some embodiments, the polymer can exclude any one or any combination of the aforementioned polymers.

The solvent should be capable of dissolving the polymer at the concentration desired in the coating solution. Solvents useful for forming the coating compositions of the present invention are chosen based on factors such as, for example, the solubility of the one or more polymers in the solvent, compatibility with the active agents, the volatility of the solvent, and the ability of the solvent to be removed from the coating layer after the coating layer configuration is fixed. Any suitable solvent, or mixture of solvents, that meets the criteria for a coating solvent can be used.

Examples of suitable solvents for the practice of the present invention include, but are not limited to, dimethylacetamide, dimethylformamide, tetrahydrofuran, cyclohexanone, acetone, acetonitrile, i-propanol, n-propanol, methanol, ethanol, butanol, propylene glycol monomethyl ether, methyl butyl ketone, methyl ethyl ketone, diethyl ketone, ethyl acetate, n-butyl acetate, dioxane, chloroform, water (buffered saline), dimethylsulfoxide, dimethylformide, benzene, toluene, xylene, hexane, cyclohexane, pentane, heptane, octane, nonane, decane, decalin, i-butyl acetate, i-propyl acetate, diacetone alcohol, benzyl alcohol, 1-butanone, 2-butanone, N-methylpyrrolidinone, methylene chloride, carbon tetrachloride, tetrachloroethylene, tetachloroethane, chlorobenzene, 1,1,1-trichloroethane, formamide, hexafluoroisopropanol, 1,1,1-trifluoroethanol, hexamethyl phosphoramide, and combination thereof.

The drug or therapeutic agent includes agents that have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration or proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include 40-epi-(N-1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Ith/IIIa platelet membrane receptor antagonist antibody, recombinant hirudin, thrombin inhibitors such as ANGIOMAX™ (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, or combinations thereof. Examples of cytostatic substances include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

Application of Coating Composition onto a Medical Device.

Application of the coating composition onto the medical device can be accomplished by any method known in the art. For example, the coating composition may be applied to the medical device by casting, spraying, dipping or immersing, direct dispensing by hand or injection. The coating compositions of the present invention may be applied to all or to selected surfaces of a device.

Operations such as wiping, centrifugation, blowing or other web-clearing acts may be performed to achieve a more uniform coating. Briefly, wiping refers to physical removal of excess coating from the surface of the device; centrifugation refers to the rapid rotation of the device about an axis of rotation; and blowing refers to application of air at a selected pressure to the deposited coating. Excess coating may also be vacuumed off the surface of the device.

Before applying the coating layer to a medical device, the surface of the device should be clean and free from contaminants that may be have been introduced during manufacture. However, no particular surface treatment is required prior to applying the coating composition. Metallic surfaces of stents can, for example, be cleaned by an argon plasma process as is known to one of ordinary skill in the art.

A primer layer may optionally be used in the embodiments of the present invention to aid the adhesion of the coating layer to the device surface. This is particularly useful when the presence or concentration of the active agent in the polymer matrix interferes with the ability of the polymer matrix to adhere effectively to the device surface. If an optional primer layer is used, the primer layer is coated on the device or a portion of the device by any method described herein or known to one of ordinary skill in the art. The primer layer is dried (solvent removed) or cured before the coating composition comprising the polymer matrix and active agent is applied to the surface of the primer layer. Primer compositions may be prepared by adding a predetermined amount of one or more polymers to a predetermined amount of solvent or mixture of solvents. Representative examples of polymers for the primer layer include, but are not limited to, polyisocyanates, polyethers, polyurethanes, acrylates, titanates, zirconates, silane coupling agents, high amine content polymers, polymers with a high content of hydrogen bonding groups, and unsaturated polymers and prepolymers. Representative examples of polymers also include those polymers used in the polymer matrices of the present invention as described herein. Further examples of primer layers useful for the medical devices of the present invention include those disclosed in U.S. Pat. No. 6,908,624 to Hossainy et al., the disclosure of which is incorporated herein by reference.

Drying Coating Compositions

After coating the medical device and before or after the freeze-thaw cycle process, solvent remaining in the wet coating layer is removed to form, a dry coating layer. It is understood that by drying substantially all the solvent will be removed from the coating layer, but traces or residues can remain blended with the polymer. In order not to change the fixed morphology of the active agent in the coating layer, the selected method should remove the solvent without causing undesired phase separations or phase changes. Suitable methods for removing the solvent from the coating composition include, but are not limited to, evaporation, freeze-drying (sublimation), non-solvent exchange, critical point drying, or any combination thereof. Removal of the solvent may occur in a controlled atmosphere, for example humid, anhydrous or solvent saturated, at ambient pressure or under vacuum. The temperature at which the solvent is removed will depend on the method, and may vary over a wide range.

In one embodiment of the present invention, solvent in the wet coating layer is removed by freeze-drying. The method comprises first freezing the coating layer, if the layer is not already in a frozen state, and then placing the medical device under reduced pressure or in a vacuum so that the solvent molecules vaporize (sublime) without the solvent passing through a liquid phase. The rate at which the coating layer is frozen and solvent removed may vary over a wide range. In one embodiment, the coating layer is frozen to 0° C. or less, alternatively to −40° C. or less, −70° C. or less, −100° C. or less, and −150° C. or less. In some embodiments, solvent removal is in essence accomplished under the freeze part of the freeze-thaw cycle of the present invention.

Evaporation of the solvent can occur at room temperature or can be induced by heating the device to a temperature for a period of time. Removal of the solvent may also occur in a controlled atmosphere, for example humid, anhydrous or solvent saturated, at ambient pressure or under vacuum. Conditions should be chosen so that they do not substantially adversely affect the active agent or the configuration of the active agent. The coating layer can be heated at a temperature for a period of time, for example, at 60° C. for 10 to 24 hours. The heating temperature is chosen so as not to exceed temperatures at which the active agent is adversely affected.

In yet another embodiment of the present invention, solvent of the coating layer can be removed from the coating layer by exchange with a non-solvent for the active agent, and subsequent removal of the non-solvent. This can be accomplished, for example, by exposing the wet polymer-matrix-active-agent coating layer to the non-solvent. The chosen non-solvent should be miscible with the solvent of the coating composition. In some invention embodiments, the non-solvent is substantially miscible with the coating composition solvent. Examples of suitable non-solvents for the active agents include, but are not limited to, supercritical $CO_2$, isopropyl alcohol, acetone, heptane and hexane, and blends thereof. Other examples of suitable solvents include, but are not limited to, fluorocarbons and chlorofluorocarbons, for example Freon™ and HCFC 141b (dichlorofluoroethane), and blends of fluorocarbons and alcohol such as, for example, dichlorofluoroethane blended with ethanol. Non-solvent exchange may be carried out, for example, by method such as liquid, spray or vapor mist contact. In those embodiments where supercritical $CO_2$ is used as the non-solvent for the active agent, the coating layer may be dried by critical point drying. In some embodiments, the coating layers of the present invention are dried by critical point drying.

Post-Formation Processing Steps

After drying the coating layers by removing solvent from the wet coating, post-freeze-thaw treatments may be performed to the coating layers and medical devices. Optional post-processing steps include, but are not limited to, annealing the coating layer, applying a protective coating, applying a rate-reducing membrane, diffusion barrier layer or topcoat layer to the coating layer surface, applying an optional finishing coat layer, and sterilization. The medical devices may further comprise an optional top-coat or barrier layer that, in some embodiments, controls the diffusion of the active agent out of the coating layer. Outer coating layers can be applied over all or only a portion of the coating layer comprising the active agent.

Medical Devices

Throughout this application "medical device" or "medical article" are used interchangeably, and each refers to any device or article that can be used in the medical treatment of a human or veterinary subject. In some embodiments, the underlying medical device that is coated is a finished product such that the device does not need any pre-coating manufacturing steps. Medical devices may be used either externally on a subject or implanted in a subject. In a preferred embodiment, the medical device is implantable. An example of an implantable medical device is a stent, which can be implanted into a human or veterinary patient. While examples of coating a device such as a drug eluting or delivery stent are described herein, one of skill in the art will appreciate that other medical devices and substrates can be manufactured using the methods of the present invention. Examples of medical devices include, but are not limited to, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts vena cava filters, and endocardial leads. Examples of stents include, but are not limited to, tubular stents, self-expanding stents, balloon expandable stents, coil stents, ring stents, multi-design stents, and the like. In some embodiments, the stents include, but are not limited to, vascular stents, renal stents, biliary stents, pulmonary stents and gastrointestinal stents.

The underlying structure of the medical device can be virtually any design. The medical device can be comprised of a metallic material or alloy, low-ferromagnetic, non-ferromagnetic, biostable polymeric, biodegradable polymeric, bioabsorbable polymers, biodegradable metallic or other compatible material known in the art. Examples of metals and alloys include, but are not limited to, ELASTINITE®, NITINOL® (Nitinol Devices and Components, Fremont, Calif.), stainless steel, tantalum, tantalum-based alloys, nickel-titanium alloys, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc., Elgin, Ill.; MP35N and MP20N, SPS Technologies, Jenkintown, Pa.) or combinations thereof. The trade names "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum.

Example

The following experiment was conducted to determine the effects of low temperature exposure on the drug recovery and drug release characteristics of stents coated with Solef and EVAL. Two types of coating were used: Type 1 included PBMA primer and Solef/everolimus drug layer; and Type 2 included EVAL primer and EVAL/everolimus drug layer.

| Group | Number of Stents Used | Type of Stent | Freeze Cycle |
| --- | --- | --- | --- |
| 1 | 6 | Type 1 | No |
| 2 | 6 | Type 1 | 30 seconds in liquid nitrogen |
| 3 | 6 | Type 2 | No |
| 4 | 6 | Type 2 | 30 seconds in liquid nitrogen |

After coating and drying of the coating in an oven, the stents were dipped in liquid nitrogen followed by application of heat at about 50 deg. C. (±3 deg. C.). The following procedure was followed: (1) Each stent was numerically identified and placed individually on a hook stainless steel mandrel; (2) 200 ml liquid nitrogen was attained from a storage tank and placed into a 500 ml liquid nitrogen container; (3) the first group of four units were dipped simultaneously into the liquid nitrogen filled container and digitally timed for 30 seconds; (4) the first group was then removed and placed in front of a heated air flow having a temperature of 50 deg. C. for 30 seconds; (4) the procedure was repeated for the second group; and (5) the units were then placed in capped vials for stent testing. Condensation formed was removed by tapping and "whiffing" the mandrel.

The results are as follows:

| Group | Sample # | Total content of everoliomus (ug) measured | Total content (ug) theoretical | % Recovery | % Average Recovery | % Relative Standard Deviation |
| --- | --- | --- | --- | --- | --- | --- |
| 1 | 1 | 52.97 | 65.08 | 81.4 | 81.5 | 0.6 |
|   | 2 | 54.38 | 66.27 | 82.1 |   |   |
|   | 3 | 52.71 | 64.92 | 81.2 |   |   |
| 2 | 4 | 52.47 | 65.93 | 79.6 | 80.5 | 1.1 |
|   | 5 | 53.85 | 66.27 | 81.3 |   |   |
|   | 6 | 53.34 | 66.10 | 80.7 |   |   |
| 3 | 7 | 83.92 | 135.00 | 62.2 | 62.3 | 0.5 |
|   | 8 | 81.85 | 130.75 | 62.6 |   |   |
|   | 9 | 78.45 | 126.50 | 62.0 |   |   |
| 4 | 10 | 81.83 | 126.00 | 64.9 | 64.2 | 2.1 |
|   | 11 | 78.84 | 125.75 | 62.7 |   |   |
|   | 12 | 80.69 | 124.00 | 65.1 |   |   |

FIG. 1 illustrates the release profile. As seen by the graph, the release rate of everolimus from the chilled Type 1 stents is about one third to that of the control. Everolimus also released more slowly from the chilled Type 2 group as compared to the control. Accordingly, the freeze-thaw cycle slowed down drug release rate while not reducing drug recovery.

While particular embodiments of the present invention have been described, it will be obvious to those skilled in the art that changes and modifications can be made without departing from the spirit and scope of the teachings and embodiments of this invention. One skilled in the art will appreciate that such teachings are provided in the way of example only, and are not intended to limit the scope of the invention. Therefore, the appended claims are to encompass within their scope all such changes and modifications as fall within the true spirit of this invention.

The invention claimed is:

1. A method comprising:
   (a) preparing a coating composition comprising one or more polymers, one or more solvents, and optionally one or more active agents;
   (b) applying the coating composition onto a medical device to form a wet coating layer;
   (c) removing the solvent(s) to form a dry coating layer, the dry coating layer having less than 2% solvent(s);
   (d) subjecting the dry coating layer to a freeze-thaw cycle; and
   (e) applying at least one additional coating layer to the medical device after the freeze-thaw cycle.

2. The method of claim 1 wherein the freeze part of the freeze-thaw cycle comprises dipping the dry coating into liquid nitrogen.

3. The method of claim 1 wherein the freeze or thaw part of the freeze-thaw cycle comprises exposing the dry coating layer to a gas at a selected freeze or thaw temperature.

4. The method of claim 1 additionally comprising removing condensation from the dry coating layer during or after the thaw part of the freeze-thaw cycle.

5. The method of claim 1 wherein the freeze part of the freeze-thaw cycle comprises dipping the medical device in a bath of dry ice, liquid argon, or liquid ammonia.

6. The method of claim 1 wherein the coating composition does not include any active agents.

7. The method of claim 1 wherein the medical device is a stent.

8. The method of claim 1 wherein the dry coating layer has less than 1% solvent(s).

9. The method of claim 1 wherein the thaw part of the freeze-thaw cycle comprises applying a gas at a temperature above 25° C. to the dry coating layer.

10. The method of claim 1 wherein the coating composition does not include any active agents and forms a topcoat over a drug layer.

11. A method comprising:
    (a) preparing a coating composition comprising one or more polymers, one or more solvents, and optionally one or more therapeutic agents;
    (b) applying the coating composition onto a medical device to form a wet coating layer;

(c) removing the solvent(s) to form a dry coating layer, the dry coating layer having less than 2% solvent(s); and (d) subjecting the dry coating layer to at least two freeze-thaw cycles.

12. The method of claim 1, wherein the freeze-thaw cycle is carried out in a chamber capable of temperature cycling.

13. The method of claim 11, wherein the freeze part of at least one of the freeze-thaw cycles comprises dipping the dry coating into liquid nitrogen.

14. The method of claim 11, wherein the freeze or thaw part of at least one of the freeze-thaw cycles comprises exposing the dry coating layer to a gas at a selected freeze or thaw temperature.

15. The method of claim 11, wherein the freeze part of at least one of the freeze-thaw cycles comprises dipping the medical device in a bath of dry ice, liquid argon, or liquid ammonia.

16. The method of claim 11, wherein the medical device is a stent.

17. The method of claim 11, wherein the dry coating layer has less than 1% solvent(s).

18. The method of claim 11, wherein the thaw part of at least one of the freeze-thaw cycles comprises applying a gas at a temperature above 25° C. to the dry coating layer.

19. The method of claim 11, wherein the coating composition does not include any therapeutic agents and forms a topcoat over a drug layer.

* * * * *